United States Patent [19]

Brancel et al.

[11] Patent Number: 5,160,343

[45] Date of Patent: Nov. 3, 1992

[54] SURGICAL INSTRUMENTS HANDLE AND FORCEPS ASSEMBLY

[75] Inventors: Dale H. Brancel, Colleyville; Michael W. Freitas, Irving; Clarence D. Zierhut, Garland, all of Tex.

[73] Assignee: Dexide, Inc., Fort Worth, Tex.

[21] Appl. No.: 756,570

[22] Filed: Sep. 9, 1991

[51] Int. Cl.5 .............................................. A61B 17/28
[52] U.S. Cl. ..................................... 606/205; 128/751
[58] Field of Search ............................. 606/205–210, 606/174, 83, 191; 128/750–755

[56] References Cited

U.S. PATENT DOCUMENTS

| 2,669,991 | 2/1954 | Curutchet | 606/205 |
| 4,493,319 | 1/1985 | Polk et al. | 606/141 |
| 4,944,093 | 7/1990 | Falk | 606/205 |
| 5,002,557 | 3/1991 | Hasson | 606/191 |

Primary Examiner—C. Fred Rosenbaum
Assistant Examiner—William Lewis
Attorney, Agent, or Firm—Jackson & Walker

[57] ABSTRACT

A surgical instruments handle, instrument head and forceps assembly for use in, preferably, endoscopic surgery through an endoscopic trocar are disclosed. The handle is contoured so as to provide a receptacle for a plurality of human fingers and a trigger-like extension for another finger as the thumb of the operator is snugly received within a ring of an instrument operator carried by the handle housing. The instrument handle extends to a tubular body of a forceps having first and second cutting members. The handle and forceps assembly may be introduced through an endoscopic locking trocar having a sleeve, having a diameter which is selectively expandable when the trocar is inserted through the abdominal wall into an abdominal cavity, during endoscopic surgery.

7 Claims, 3 Drawing Sheets

SURGICAL INSTRUMENTS HANDLE AND FORCEPS ASSEMBLY

BACKGROUND OF THE INVENTION (1) Field of the Invention

The invention relates to surgical instruments and, in particular, to a surgical instruments handle and instruments assembly which may be preferably utilized in endoscopic surgery, and being insertible through an endoscopic locking trocar during such surgery.

(2) Brief Description of the Prior Art

Surgical procedures require considerable touch and feel of the surgeon in the operation of the particular surgical instrumentation in order to satisfactorily and carefully accomplish the desired objective of the surgical procedure Accordingly, surgical instruments must incorporate into their design and operability, the ability of the surgeon to rely on simple touch techniques for activation of the instruments. Additionally, such instruments should also be designed to avoid or reduce strain upon the arms, hands and fingers of the surgeon.

Such objectives are particularly critical with respect to endoscopic surgical instruments. Endoscopic procedures gain access to the inside of an anatomical cavity by using an implement, such as a trocar, cannula, or a needle having a sharpened point to pierce or puncture the bodily tissues, muscles, membranes, or the like, which may form a portion or surround the cavity wall. A surgical needle, for example, connected to a catheter may be used to pierce a cavity in a blood vessel, subarachnoid space, heat ventricle or the like. After piercing such cavity, the needle is left in situ and used to inject or withdraw gases or liquid-phase fluids from the cavity, or to insufflate the cavity by injection of, for example, a particular inert gas or other fluid.

Similarly, in many endoscopic procedures, a small incision may be made in the skin of a patient, along the abdomen, for example, and the sharp point of a larger penetrating implement, such as a trocar of suitable length and diameter, is inserted into the incision and pushed until the point punctures the cavity wall. Therefore, a sleeve is slid over the exterior surface of the implement into the puncture wound to serve as a lining for preserving the shape of the passageway created by the implement. After the sleeve is in place, the implement may be withdrawn and an endoscope, forceps, and other surgical instruments may be inserted via the sleeve to view and operate upon organs within the cavity.

Since the area in which the surgeon must perform procedures incorporating endoscopic surgical instrumentation is smaller than that normally encountered when conventional surgical techniques are employed, reliance by the surgeon upon his touch and feel during the surgery becomes even more critical, and surgical instrumentation must take this factor into consideration such that touch and feel are transferred between the surgeons hand and the fingers through the instrument and between the are of operation with the abdomen and the surgeon's hand.

Many surgical instruments for use in endoscopic and conventional surgical procedures, such as forceps and other cutting instruments, incorporate a pistol-like handle. Typical of such prior art pistol-like handles is that as shown and described in U.S. Pat. No. 5,026,375, entitled "Surgical Cutting Instrument". Many such instruments include a protrusion or abutment on the pistol-like handle in order to receive the thumb of the surgeon. Accordingly, such instruments may not maximize surgical touch and feel between the area of surgery and the surgeon's hand.

The present invention addresses the problems and the deficiencies of the prior art, as discussed above.

SUMMARY OF THE INVENTION

A surgical instruments handle and forceps assembly is provided, having particular use in endoscopic surgery procedures wherein the forceps are introduced through a surgical trocar into the abdomen. The surgical instruments handle comprises a body having forward and rearward sides. A receptacle is defined on the forward side of the body for acceptance therethrough of a plurality of fingers of a human operator. A trigger-like abutment is provided immediate the lower end of the handle for engageable finger contact as the body is held by the human operator. Means are provided for receipt of a surgical instrument body, such as that for forceps or the like, immediate to the upper end of the handle, with the surgical instrument body having an instrument manipulator disposed through the receiving means and engageable by the handle. A thumb-activator within the surgical instrument operator has first and second ends, with the surgical instrument operator being pivotally secured to the body on the body rearward side. Means are provided on the operator at the operator's first end for operationally engaging the manipulator. A ring is defined on the second end of the operator for introduction therethrough and snug engagement thereof of a thumb of the human operator. The ring may be pivotally secured to the second end of the operator.

In combination with the handle, a forceps component is carried on the handle and includes a tubular body having a first end extending from the handle. The instrument manipulator is housed within the body and has one end secured and extending to the instrument operator. A series of surgical forceps members are provided and are selectively moveable between open and closed positions upon movement of the instrument operator relative to the handle. The forceps members may comprise first and second cutting members, one of the cutting members being pivotally secured relative to the tubular body, and the second of the cutting members being contourally companionably defined at the second end of the tubular body.

The instruments handle and instrument head assembly may be utilized in endoscopic surgical proceedings incorporating the additional component in the apparatus of a trocar having a trocar sleeve with a through passage and a first end extendable into the abdominal cavity through an incision in the abdominal wall, with the first end having a first external dimension for passage through the incision. Means are provided in the trocar component of the apparatus for expanding a portion of the first end of the trocar sleeve within the abdominal cavity so that the external dimension of the first end of the trocar sleeve within the cavity is expanded to a larger, second external dimension. The first end of the trocar sleeve, when the sleeve is expanded to the second dimension, will abut the inner abdominal wall about the incision when so expanded to the second external dimension to resist withdrawal of the trocar sleeve from the abdominal cavity.

DESCRIPTION OF THE DEFERRED EMBODIMENTS

Figure 1:
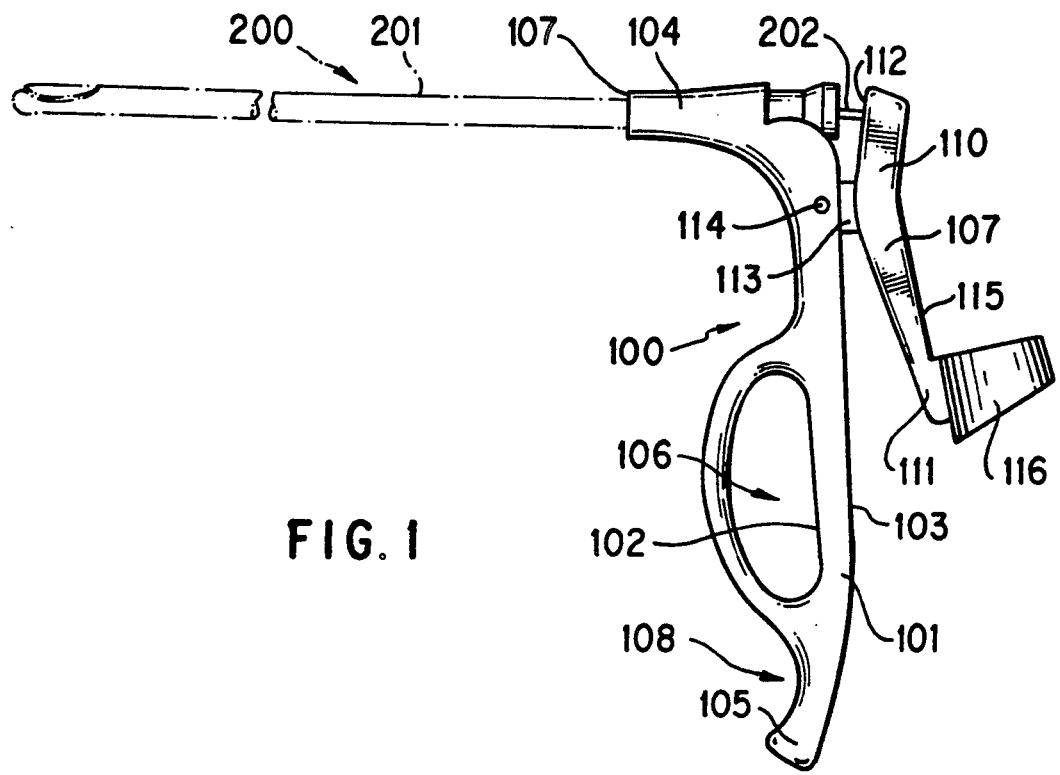
FIG. 1 is a side view of the combination surgical instruments handle and forceps assembly.

With reference to FIG. 1, there is shown the apparatus of the present invention, basically comprising an instrument body 200 secured at one end to a surgical instrument's handle 100.

The surgical instrument's handle 100 receives the rearward end of the instrument body 200 through a protrusion 107 defined through the upper end 104 of a surgical instrument's handle 101. The handle body 101 has a smooth extending forward side 102 and a comparatively straight rearward side 103 extending to a slightly forwardly sloping lower end portion 105 defining a trigger like abutment 108 for receipt of the smallest finger F-4 of the hand H of a surgeon (FIG. 2).

The handle body 101 has a forwardly extending arc-like enclosure 125 facing forwardly to define a finger receptacle 106 (FIG. 3) for entry of fingers F-2 and F-3 of the hand H of the surgeon around the smooth surface of the forward side 102 of the handle body 101, as the apparatus 100 is grasped and manipulated by the surgeon.

A manipulator 202, such as a tube, cable, wire, or the like, extending through the instrument body 200 extends out of the hole 107 at the upper end 104 of the handle body 101 and is secured by securement 112, such as threads, glue, pins, or the like, immediate the upper end 110 of a thumb activated operator 109 partially extending down the rearward side 103 of the handle body 101. The thumb activated operator 109 is secured by means of pivot 113 and a pivot pin 114 to the handle body 101.

Figure 2:
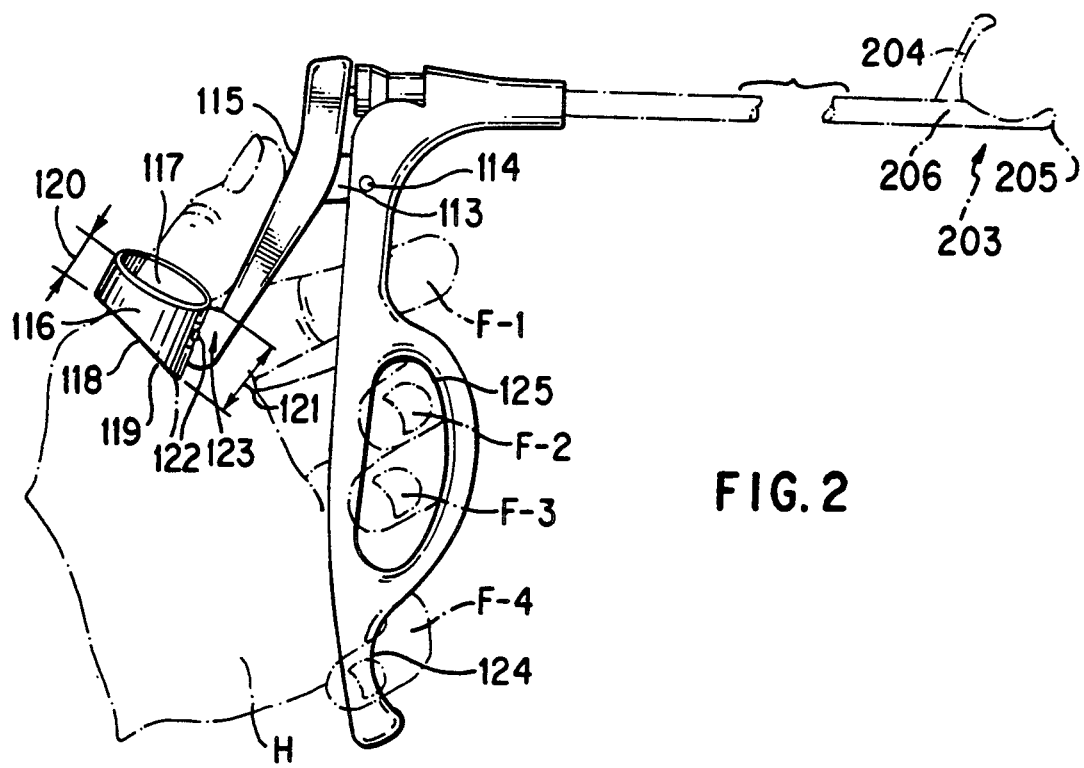
FIG. 2 is a view of the handle and forceps assembly similar to that shown in FIG. 1, showing the opposite side of the surgical instruments handle in the hand of a surgeon with the forceps instrument end being shown in open position.
Figure 3:
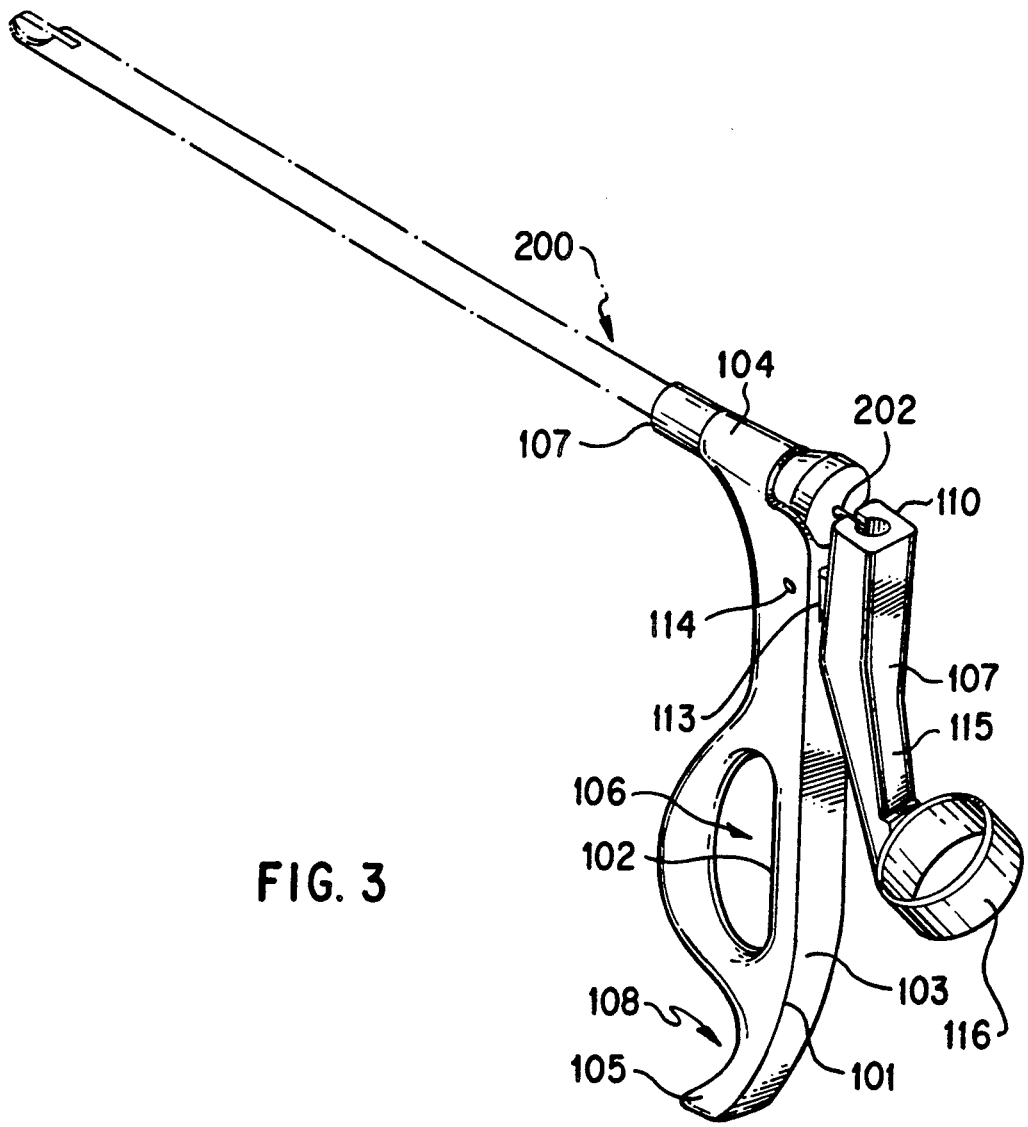
FIG. 3 is a prospective view of the surgical instruments handle and the forceps assembly with the ring member being slightly pivoted.
Figure 4:
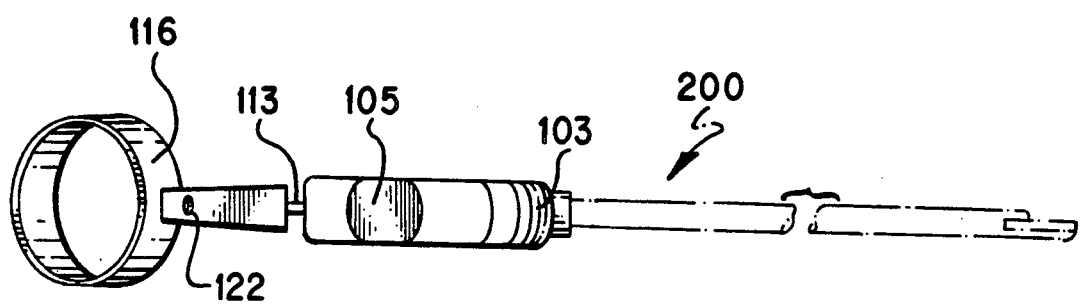
FIG. 4 is a top planar view, looking downwardly, of the surgical instruments handle and forceps assembly.

A thumb receiving profile of surface 115 is contourally defined on the operator 109 extending to a thumb receiving ring 116 secured at the lower end 111 of the thumb activated operator 109 by means of contoured pivot pin 123 in pivot receptacle 122, such that the ring 116 may pivot slightly to comfortably and snugly engage the thumb T on the hand H of the surgeon, the pivot of the ring 116 about the lower end 111 of the thumb activated operator 109 being selective, such as 120° from alignment of the ring 116 with the operator 109 in the position as shown in FIG. 2 to the position of the ring 116 relative to the operator 109 as shown in the position of the FIG. 3.

The ring 116 has a rearwardly extending open end 118 through which the thumb T is introduced into the ring 116, and a frontal open end 117 for movement of the thumb T of the hand H onto the thumb receiving profile surface 115. The rear open end 118 of the ring 116 is arcingly contoured, slightly, such that the width 120 of the ring 116 between the open ends 118, 117, is slightly less than the width 121 between the ends 118, 117, at the securement of the ring 116 to the operator 109 in order to provide additional comfort and communication of touch between the surgeon's hand H and thumb T and the area of surgical operation within the patient. Thus, the width 120 and width 121 result in an angled receptacle surface 119 formed at the frontal end 118 of the ring 116.

The trigger-like abutment 108 provides a smooth arcing trigger surface 124 for smooth wrap-around-like receipt of the trigger finger F-4 of the hand H of the surgeon.

The instrument body 200 has an exterior cylindrical tubular body 201 which extends through the protrusion 107 in the upper end 104 of the body 101 of the handle 100. At the outboard-end of the instrument body 200 is an instrument head, such as forceps 203 having first and second cutting members 204, 205 thereon. The cutting member 204 is secured at pivot securement 206 to the tubular body 20; and the cutting member 205 is profiled on the outboard-most end of the tubular body 201. The forceps 203 are secured to the outboard-most end of the manipulator 202.

Figure 5:
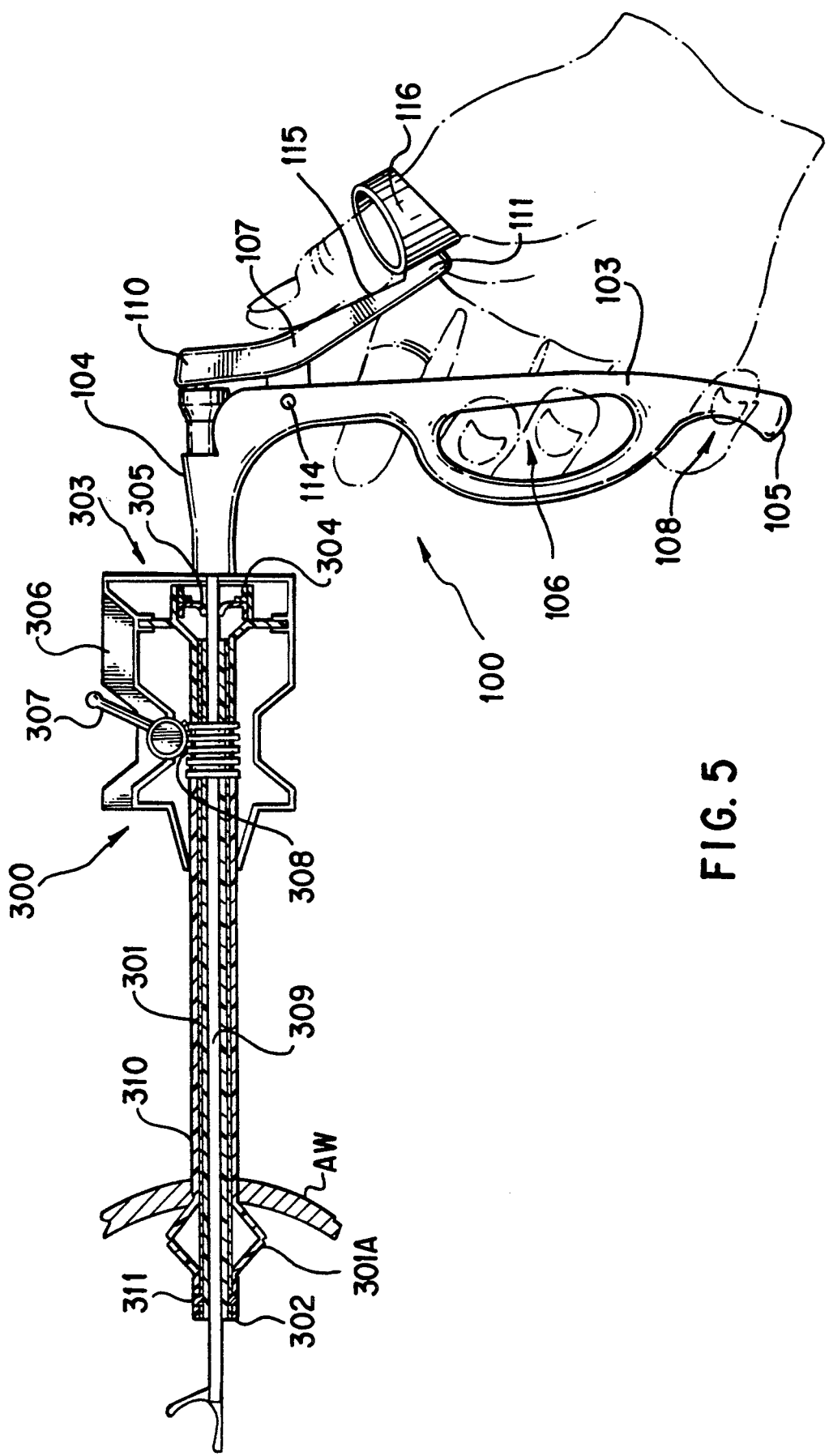
FIG. 5 is a side, partial sectional, view of the surgical instruments handle and forceps assembly shown in position through an endoscopic surgical trocar assembly locked interior of an abdominal wall by selective expansion of a sleeve during surgery, with the forceps assembly being shown in the hand of a surgeon.

Now with reference to FIG. 5, the apparatus includes the instrument body 200 and the surgical instruments handle 100 and is shown inserted within an abdominal wall AW by means of a trocar 300.

The trocar 300 may be an endoscopic trocar assembly, but preferably, is a locking trocar having an exterior selectively expandable sleeve member for locking engagement within the abdominal wall AW, during surgery.

As shown in FIG. 5, the trocar 300 consists of an outer sleeve 301 having an expanding component 301A at its outboard-most end. The trocar 300 also has an inner sleeve 309 and may have an electrical insulator 310 to avoid electrical shock in the event that the trocar 300 is utilized in electro-surgical operations. The sleeves are secured, one to another, by securement 311 at the forward end 302 at the outboard-most end of the trocar 300. The sleeves 301 and 309, as well as insulator 310, extend through a housing 306 having a thumb-manipulatable operator 307 extending thereon, such that the sleeve 301A may be selectively manipulated between retracted and expanded positions by means of movement of the operator 307 relative to gearmesh members 308, 310. The apparatus is introduced into the trocar 300 through a open rearward end 303 and into a seal assembly 305 which prevents escape of gas during insufflation.

As stated above, the handle 100 may be utilized with a number of surgical instruments well known to those skilled in the art, and such instrument may take the form of instrument body 200 and forceps 203. The handle 100 and secured instrument 200 have particular utility in endoscopic operations, where the combined apparatus will be introduced into the abdominal wall AW through use of a trocar 300. In such event, the handle 100 and instrument body 200 are secured together, and the trocar 300 is emplaced into the abdominal wall, AW, as described above. Thereafter, the hand H of the surgeon grasps the surgical instrument handle 100 by introducing one or more of the fingers F-2, F-3 through the arc-like enclosure portion 125 and positioning them in the finger receptacle 106 as the first finger F-1 grasps the handle 100 thereabove and the trigger finger F-4 is emplaced upon the trigger surface 124 of the trigger-like abutment 108. The thumb T of the hand H of the surgeon is introduced through the rear open end 118 through the ring 116 and out the frontal open end 117 for placement onto the thumb receiving profiled surface 115. Now, the apparatus, with the forceps 203 closed, is carefully introduced through the rearward end 303 of the trocar 300, through the abdominal wall AW and out the forward end 302 of the trocar 300.

Now, the surgeon may manipulate the forceps 203 by manipulation of the apparatus to move the cutting members 204, 205, into cutting and release positions by slowly manipulating the operator 109 by slight application of pressure by the thumb T on the surface 115 of the operator 109 to manipulate the forceps 203 by relative movement of the manipulator 202 to the tubular body 201. The pivot securement 122, 123, of the ring 116 to the operator 109 permits the thumb T to be moved relative to the operator 109, slightly, to accommodate thumb length, curvature, and the like to further enable the surgeon to accommodate and feel touch during surgery, and to otherwise provide for the comfort of the surgeon during the surgical operation and manipulation of the apparatus.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit invention.

What is claimed and desired to be secured by Letters Patent is:

1. A surgical instruments handle, comprising:
   (1) a body having forward and rearward sides;
   (2) a receptacle defined on the forward side of said body for acceptance therethrough of a plurality of fingers of a human operator;
   (3) a trigger-like abutment immediate the lower end of said handle for engagable finger contact as the body is held by the human operator;
   (4) means for receipt of a surgical instrument body immediate the upper end of said handle, said surgical instrument body having an instrument manipulator disposed through said receiving means and engagable by said handle;
   (5) a thumb-activatable surgical instrument operator having first and second ends, said surgical instrument operator being pivotally secured to said body on said body rearward side;
   (6) means on said operator at said operator's first end for operationally engaging said manipulator to said operator; and
   (7) a ring defined on the second end of said operator for introduction therethrough and snug engagement therein of a thumb of the human operator, said ring being pivotally secured to said second end of said operator.

2. A combination surgical instruments handle and forceps assembly, comprising:
   (1) a handle having forward and rearward sides;
   (2) a receptacle defined on the forward side of said handle for acceptance therethrough of a plurality of fingers of a human operator;
   (3) a trigger-like abutment immediate the lower end of said handle for engagable finger contact as the handle is held by a human operator;
   (4) means for receipt of a forceps tubular body immediate the upper end of said handle;
   (5) a thumb-activatable surgical instruments operator having first and second ends pivotally secured to said handle on its rearward side;
   (6) means on said operator at said operator's first end for operationally engaging said forceps to said operator;
   (7) a ring defined on the second end of said operator for introduction therethrough and snug engagement therein of a thumb of the human operator, said ring being pivotally secured to said second end of said operator;
   (8) a forceps component carried by said instruments handle and including:
      (a) a tubular body having a first end extending from said handle;
      (b) An instrument manipulator housed within said body and having one end securely extending to said instrument operator; and
      (c) a series of surgical forceps member selectively movable between open and closed positions by said manipulator upon movement of said instrument operator relative to said handle.

3. The combination surgical instruments and forceps assembly of claim 2:
   said forceps comprising first and second cutting members, one of said cutting members being pivotally secured relative to said tubular body, and the second of said cutting members being contourly companionly defined at the second end of said tubular body.

4. A combination handle and surgical instruments assembly, comprising:
   (1) a handle body having forward and rearward sides;
   (2) a receptacle defined on the forward side of said body for acceptance therethrough of a plurality of fingers of a human operator;
   (3) a trigger-like abutment immediate the lower end of said handle for engagement finger contact as the body is held by the human operator;
   (4) means for receipt of a surgical instrument body immediate the upper end of said handle, said surgical instrument body including:
      (a) a tubular housing having a first end extending from said handle;
      (b) an instrument manipulator housed within said tubular body and having one end securely extending to said instrument operator and the other end defining a surgical instrument head, said instrument manipulator being disposed through said receiving means and engagable by said handle;
   (5) a thumb-activatable surgical instrument operator having first and second ends pivotally secured to said body on its rearward side;
   (6) means of said operator at its first end for operationally engaging said manipulator to said operator; and
   (7) a ring defined on the second hand of said operator for introduction therethrough and snug engagement therein of a thumb of the human operator, said ring being pivotally secured to said second end of said operator.

5. A combination endoscopic surgical instruments handle and instrument head assembly, comprising:
(1) a trocar including a tubular housing;
(2) a trocar sleeve having a through passage, and a first end extendable into an abdominal cavity through an incision in the abdominal wall, the first end having a first external dimension for passage through the incision;
(3) mechanical drive means for telescopically shifting said trocar sleeve so that the eternal dimension of the first end of said trocar sleeve within the cavity is expanded to a larger, second external dimension, the first end of said trocar sleeve abutting the inner abdominal wall about the incision when expanded to the second external dimension to resist withdrawal of the trocar sleeve from the abdominal cavity;
(4) an endoscopic surgical instruments handle and instrument head, said head being introducible through said trocar, while said trocar is in the expanded position within said abdominal wall, said instruments handle comprising:
  (a) a body having forward and rearward sides;
  (b) a receptacle defined on the forward side of said handle body for acceptance therethrough of a plurality of fingers of a human operator;
  (c) a trigger-like abutment immediate the lower end of said handle for engagable finger contact as the handle body is held by the human operator;
  (d) means for receipt of said surgical instrument head immediate the upper end of said handle, said surgical instrument head having an instrument manipulator disposed through said receiving means and engagable by said handle;
  (e) a thumb-activatable surgical instrument operator having first and second ends pivotally secured to said handle body on said handle body's rearward side;
  (f) means on said operator at said operator's first end for operationally engaging said manipulator to said operator; and
  (g) a ring defined on the second end of said operator for introduction therethrough and snug engagement therein of a thumb of the human operator, said ring being pivotally secured to said second end of said operator.

6. The apparatus of claim 5 wherein said instrument head comprises surgical forceps, said surgical forceps comprising:
(1) a tubular body having a first end extending from said handle;
(2) an instrument manipulator housed within said handle body and having one end securely extending to said instrument operator;
(3) a series of surgical forceps members selectively movable between open and closed positions by said manipulator upon movement of said instrument operator relative to said handle body.

7. The apparatus of claim 6, said forceps comprising first and second cutting members, one of said cutting members being pivotally secured relative to said tubular body and the second of said cutting members being contourly companionably defined at the second end of said tubular body.

* * * * *